(12) United States Patent
Neville

(10) Patent No.: US 11,098,120 B2
(45) Date of Patent: Aug. 24, 2021

(54) IMMUNOMODULATION BY ANTI-CD3 IMMUNOTOXINS TO TREAT CANCERS BEARING OR NOT UNIFORMLY BEARING SURFACE CD3

(71) Applicant: ANGIMMUNE, LLC, Bethesda, MD (US)

(72) Inventor: David M. Neville, Bethesda, MD (US)

(73) Assignee: ANGIMMUNE, LLC, Bethesda, MD (US)

( * ) Notice: Subject to any disclaimer, the term of this patent is extended or adjusted under 35 U.S.C. 154(b) by 407 days.

(21) Appl. No.: 16/153,047

(22) Filed: Oct. 5, 2018

(65) Prior Publication Data

US 2019/0023789 A1 Jan. 24, 2019

Related U.S. Application Data

(63) Continuation of application No. 14/390,885, filed as application No. PCT/US2013/030658 on Mar. 13, 2013, now abandoned.

(60) Provisional application No. 61/687,241, filed on Apr. 20, 2012.

(51) Int. Cl.

| | |
|---|---|
| *A61K 47/68* | (2017.01) |
| *C07K 16/28* | (2006.01) |
| *A61K 38/16* | (2006.01) |
| *C07K 16/30* | (2006.01) |
| *A61P 35/00* | (2006.01) |
| *A61K 39/00* | (2006.01) |
| *A61K 39/395* | (2006.01) |

(52) U.S. Cl.
CPC ........ *C07K 16/2809* (2013.01); *A61K 38/164* (2013.01); *A61K 39/0011* (2013.01); *A61K 39/3955* (2013.01); *A61K 47/6829* (2017.08); *A61K 47/6849* (2017.08); *A61K 47/6879* (2017.08); *A61P 35/00* (2018.01); *C07K 16/30* (2013.01); *A61K 2039/505* (2013.01); *A61K 2039/545* (2013.01); *C07K 2317/35* (2013.01); *C07K 2317/622* (2013.01); *C07K 2317/73* (2013.01); *C07K 2319/00* (2013.01); *Y02A 50/30* (2018.01)

(58) Field of Classification Search
None
See application file for complete search history.

(56) References Cited

U.S. PATENT DOCUMENTS

2005/0033034 A1* 2/2005 Engel ............... A61K 39/39541
530/391.1

OTHER PUBLICATIONS

Naresh et al. (Leukemia & Lymphoma, Aug. 2004 vol. 45 (8), pp. 1569-1577). (Year: 2004).*
D'Amore et al. (Br J Haematol. Sep. 2010;150(5):565-73). (Year: 2010).*

* cited by examiner

*Primary Examiner* — Zachary S Skelding
(74) *Attorney, Agent, or Firm* — W&C IP

(57) ABSTRACT

Methods of modulating the immune systems of patients suffering from cancers that do not bear, or do not uniformly bear, surface CD3 are provided. The methods involve administering an anti-CD3 immunotoxin (e.g. A-dmDT390-bisFv(UCHT1)), to the patient so as to cause the patient's immune system to recognize and destroy non-CD3 cancer cells.

7 Claims, 4 Drawing Sheets

Specification includes a Sequence Listing.

```
        10         20         30         40         50         60
AGADDVVDSS KSFVMENFAS YHGTKPGYVD SIQKGIQKPK SGTQGNYDDD WKGFYSTDNK 70         80         90        100        110        120
YDAAGYSVDN ENPLSGKAGG VVKVTYPGLT KVLALKVDNA ETIKKELGLS LTEPLMEQVG 130        140        150        160        170        180
TEEFIKRFGD GASRVVLSLP FAEGSSSVEY INNWEQAKAL SVELEINFET RGKRGQDAMY 190        200        210        220        230        240
EYMAQACAGN RVRRSVGSSL SCINLDWDVI RDKTKTKIES LKEHGPIKNK MSESPAKTVS 250        260        270        280        290        300
EEKAKQYLEE FHQTALEHPE LSELKTVTGT NPVFAGANYA AWAVNVAQVI DSETADNLEK 310        320        330        340        350        360
TTAALSILPG IGSVMGIADG AVHHNTEEIV AQSIALSSLM VAQAIPLVGE LVDIGFAAYN 370        380        390        400        410        420
FVESIINLFQ VVHNSYNRPA YSPGHKTQPF LPWDIQMTQT TSSLSASLGD RVTISCRASQ 430        440        450        460        470        480
DIRNYLNWYQ QKPDGTVKLL IYYTSRLHSG VPSKFSGSGS GTDYSLTISN LEQEDIATYF 490        500        510        520        530        540
CQQGNTLPWT FAGGTKLEIK GGGGSGGGGS GGGGSEVQLQ QSGPELVKPG ASMKISCKAS 550        560        570        580        590        600
GYSFTGYTMN WVKQSHGKNL EWMGLINPYK GVSTYNQKFK DKATFTVDKS SSTAYMELLS 610        620        630        640        650        660
LTSEDSAVYY CARSGYYGDS DWYFDVWGAG TTVTVSSGGG GSGGGGSGGG GSDIQMTQTT 670        680        690        700        710        720
SSLSASLGDR VTISCRASQD IRNYLNWYQQ KPDGTVKLLI YYTSRLHSGV PSKFSGSGSG 730        740        750        760        770        780
TDYSLTISNL EQEDIATYFC QQGNTLPWTF AGGTKLEIKG GGGSGGGGSG GGGSEVQLQQ 790        800        810        820        830        840
SGPELVKPGA SMKISCKASG YSFTGYTMNW VKQSHGKNLE WMGLINPYKG VSTYNQKFKD 850        860        870        880        890
KATFTVDKSS STAYMELLSL TSEDSAVYYC ARSGYYGDSD WYFDVWGAGT TVTVSS (SEQ ID NO: 1)
```

Figure 2

```
            10         20         30         40         50         60
    AGADDVVDSS KSFVMENFAS YHGTKPGYVD SIQKGIQKPK SGTQGNYDDD WKGFYSTDNK 70         80         90        100        110        120
    YDAAGYSVDN ENPLSGKAGG VVKVTYPGLT KVLALKVDNA ETIKKELGLS LTEPLMEQVG 130        140        150        160        170        180
    TEEFIKRFGD GASRVVLSLP FAEGSSSVEY INNWEQAKAL SVELEINFET RGKRGQDAMY 190        200        210        220        230        240
    EYMAQACAGN RVRRSVGSSL SCINLDWDVI RDKTKTKIES LKEHGPIKNK MSESPAKTVS 250        260        270        280        290        300
    EEKAKQYLEE FHQTALEHPE LSELKTVTGT NPVFAGANYA AWAVNVAQVI DSETADNLEK 310        320        330        340        350        360
    TTAALSILPG IGSVMGIADG AVHHNTEEIV AQSIALSSLM VAQAIPLVGE LVDIGFAAYN 370        380        390        400        410        420
    FVESIINLFQ VVHNSYNRPA YSPGHKTQPF LPWDIQMTQT TSSLSASLGD RVTISCRASQ 430        440        450        460        470        480
    DIRNYLNWYQ QKPDGTVKLL IYYTSRLHSG VPSKFSGSGS GTDYSLTISN LEQEDIATYF 490        500        510        520        530        540
    CQQGNTLPWT FAGGTKLEIK GGGGSGGGGS GGGGSEVQLQ QSGPELVKPG ASMKISCKAS 550        560        570        580        590        600
    GYSFTGYTMN WVKQSHGKNL EWMGLINPYK GVSTYNQKFK DKATLTVDKS SSTAYMELLS 610        620        630        640        650        660
    LTSEDSAVYY CARSGYYGDS DWYFDVWGAG TTVTVSSGGG GSGGGGSGGG GSDIQMTQTT 670        680        690        700        710        720
    SSLSASLGDR VTISCRASQD IRNYLNWYQQ KPDGTVKLLI YYTSRLHSGV PSKFSGSGSG 730        740        750        760        770        780
    TDYSLTISNL EQEDIATYFC QQGNTLPWTF AGGTKLEIKG GGGSGGGGSG GGGSEVQLQQ 790        800        810        820        830        840
    SGPELVKPGA SMKISCKASG YSFTGYTMNW VKQSHGKNLE WMGLINPYKG VSTYNQKFKD 850        860        870        880        890
    KATLTVDKSS STAYMELLSL TSEDSAVYYC ARSGYYGDSD WYFDVWGQGT TLTVFS (SEQ ID NO: 2)
```

Figure 3A

```
          10         20         30         40         50         60
.GADDVVDSS KSFVMENFAS YHGTKPGYVD SIQKGIQKPK SGTQGNYDDD WKGFYSTDNK 70         80         90        100        110        120
YDAAGYSVDN ENPLSGKAGG VVKVTYPGLT KVLALKVDNA ETIKKELGLS LTEPLMEQVG 130        140        150        160        170        180
TEEFIKRFGD GASRVVLSLP FAEGSSSVEY INNWEQAKAL SVELEINFET RGKRGQDAMY 190        200        210        220        230        240
EYMAQACAGN RVRRSVGSSL SCINLDWDVI RDKTKTKIES LKEHGPIKNK MSESPAKTVS 250        260        270        280        290        300
EEKAKQYLEE FHQTALEHPE LSELKTVTGT NPVFAGANYA AWAVNVAQVI DSETADNLEK 310        320        330        340        350        360
TTAALSILPG IGSVMGIADG AVHHNTEEIV AQSIALSSLM VAQAIPLVGE LVDIGFAAYN 370        380        390        400        410        420
FVESIINLFQ VVHNSYNRPA YSPGHKTQPF LPWDIQMTQT TSSLSASLGD RVTISCRASQ 430        440        450        460        470        480
DIRNYLNWYQ QKPDGTVKLL IYYTSRLHSG VPSKFSGSGS GTDYSLTISN LEQEDIATYF 490        500        510        520        530        540
CQQGNTLPWT FAGGTKLEIK GGGGSGGGGS GGGGSEVQLQ QSGPELVKPG ASMKISCKAS 550        560        570        580        590        600
GYSFTGYTMN WVKQSHGKNL EWMGLINPYK GVSTYNQKFK DKATLTVDKS SSTAYMELLS 610        620        630        640        650        660
LTSEDSAVYY CARSGYYGDS DWYFDVWGAG TTVTVSSGGG GSGGGGSGGG GSDIQMTQTT 670        680        690        700        710        720
SSLSASLGDR VTISCRASQD IRNYLNWYQQ KPDGTVKLLI YYTSRLHSGV PSKFSGSGSG 730        740        750        760        770        780
TDYSLTISNL EQEDIATYFC QQGNTLPWTF AGGTKLEIKG GGGSGGGGSG GGGSEVQLQQ 790        800        810        820        830        840
SGPELVKPGA SMKISCKASG YSFTGYTMNW VKQSHGKNLE WMGLINPYKG VSTYNQKFKD 850        860        870        880        890
KATLTVDKSS STAYMELLSL TSEDSAVYYC ARSGYYGDSD WYFDVWGQGT TLTVFS (SEQ ID NO: 3)
```

Figure 3B

SEQUENCE LISTING

<160> NUMBER OF SEQ ID NOS: 3

<210> SEQ ID NO 1
<211> LENGTH: 896
<212> TYPE: PRT
<213> ORGANISM: Artificial Sequence
<220> FEATURE:
<223> OTHER INFORMATION: Synthetic recombinant toxin molecule

<400> SEQUENCE: 1

Ala Gly Ala Asp Asp Val Val Asp Ser Ser Lys Ser Phe Val Met Glu
1               5                   10                  15

Asn Phe Ala Ser Tyr His Gly Thr Lys Pro Gly Tyr Val Asp Ser Ile
            20                  25                  30

```
Gln Lys Gly Ile Gln Lys Pro Lys Ser Gly Thr Gln Gly Asn Tyr Asp
         35                  40                  45

Asp Asp Trp Lys Gly Phe Tyr Ser Thr Asp Asn Lys Tyr Asp Ala Ala
 50                      55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
             100                 105                 110

Glu Pro Leu Met Glu Gln Val Gly Thr Glu Glu Phe Ile Lys Arg Phe
         115                 120                 125

Gly Asp Gly Ala Ser Arg Val Val Leu Ser Leu Pro Phe Ala Glu Gly
     130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                 165                 170                 175

Asp Ala Met Tyr Glu Tyr Met Ala Gln Ala Cys Ala Gly Asn Arg Val
             180                 185                 190

Arg Arg Ser Val Gly Ser Ser Leu Ser Cys Ile Asn Leu Asp Trp Asp
         195                 200                 205

Val Ile Arg Asp Lys Thr Lys Thr Lys Ile Glu Ser Leu Lys Glu His
     210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                 245                 250                 255

Glu His Pro Glu Leu Ser Glu Leu Lys Thr Val Thr Gly Thr Asn Pro
             260                 265                 270

Val Phe Ala Gly Ala Asn Tyr Ala Ala Trp Ala Val Asn Val Ala Gln
         275                 280                 285

Val Ile Asp Ser Glu Thr Ala Asp Asn Leu Glu Lys Thr Thr Ala Ala
     290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                 325                 330                 335

Ser Ser Leu Met Val Ala Gln Ala Ile Pro Leu Val Gly Glu Leu Val
             340                 345                 350

Asp Ile Gly Phe Ala Ala Tyr Asn Phe Val Glu Ser Ile Ile Asn Leu
         355                 360                 365

Phe Gln Val Val His Asn Ser Tyr Asn Arg Pro Ala Tyr Ser Pro Gly
     370                 375                 380

His Lys Thr Gln Pro Phe Leu Pro Trp Asp Ile Gln Met Thr Gln Thr
385                 390                 395                 400

Thr Ser Ser Leu Ser Ala Ser Leu Gly Asp Arg Val Thr Ile Ser Cys
                 405                 410                 415

Arg Ala Ser Gln Asp Ile Arg Asn Tyr Leu Asn Trp Tyr Gln Gln Lys
             420                 425                 430

Pro Asp Gly Thr Val Lys Leu Leu Ile Tyr Tyr Thr Ser Arg Leu His
         435                 440                 445
```

-continued

```
Ser Gly Val Pro Ser Lys Phe Ser Gly Ser Gly Ser Gly Thr Asp Tyr
        450                 455                 460
Ser Leu Thr Ile Ser Asn Leu Glu Gln Glu Asp Ile Ala Thr Tyr Phe
465                 470                 475                 480
Cys Gln Gln Gly Asn Thr Leu Pro Trp Thr Phe Ala Gly Gly Thr Lys
                485                 490                 495
Leu Glu Ile Lys Gly Gly Gly Ser Gly Gly Gly Ser Gly Gly
            500                 505                 510
Gly Gly Ser Glu Val Gln Leu Gln Gln Ser Gly Pro Glu Leu Val Lys
        515                 520                 525
Pro Gly Ala Ser Met Lys Ile Ser Cys Lys Ala Ser Gly Tyr Ser Phe
530                 535                 540
Thr Gly Tyr Thr Met Asn Trp Val Lys Gln Ser His Gly Lys Asn Leu
545                 550                 555                 560
Glu Trp Met Gly Leu Ile Asn Pro Tyr Lys Gly Val Ser Thr Tyr Asn
                565                 570                 575
Gln Lys Phe Lys Asp Lys Ala Thr Phe Thr Val Asp Lys Ser Ser Ser
            580                 585                 590
Thr Ala Tyr Met Glu Leu Leu Ser Leu Thr Ser Glu Asp Ser Ala Val
        595                 600                 605
Tyr Tyr Cys Ala Arg Ser Gly Tyr Tyr Gly Asp Ser Asp Trp Tyr Phe
610                 615                 620
Asp Val Trp Gly Ala Gly Thr Thr Val Thr Val Ser Ser Gly Gly Gly
625                 630                 635                 640
Gly Ser Gly Gly Gly Gly Ser Gly Gly Gly Gly Ser Asp Ile Gln Met
                645                 650                 655
Thr Gln Thr Thr Ser Ser Leu Ser Ala Ser Leu Gly Asp Arg Val Thr
            660                 665                 670
Ile Ser Cys Arg Ala Ser Gln Asp Ile Arg Asn Tyr Leu Asn Trp Tyr
        675                 680                 685
Gln Gln Lys Pro Asp Gly Thr Val Lys Leu Leu Ile Tyr Tyr Thr Ser
690                 695                 700
Arg Leu His Ser Gly Val Pro Ser Lys Phe Ser Gly Ser Gly Ser Gly
705                 710                 715                 720
Thr Asp Tyr Ser Leu Thr Ile Ser Asn Leu Glu Gln Glu Asp Ile Ala
                725                 730                 735
Thr Tyr Phe Cys Gln Gln Gly Asn Thr Leu Pro Trp Thr Phe Ala Gly
            740                 745                 750
Gly Thr Lys Leu Glu Ile Lys Gly Gly Gly Gly Ser Gly Gly Gly Gly
        755                 760                 765
Ser Gly Gly Gly Gly Ser Glu Val Gln Leu Gln Gln Ser Gly Pro Glu
770                 775                 780
Leu Val Lys Pro Gly Ala Ser Met Lys Ile Ser Cys Lys Ala Ser Gly
785                 790                 795                 800
Tyr Ser Phe Thr Gly Tyr Thr Met Asn Trp Val Lys Gln Ser His Gly
                805                 810                 815
Lys Asn Leu Glu Trp Met Gly Leu Ile Asn Pro Tyr Lys Gly Val Ser
            820                 825                 830
Thr Tyr Asn Gln Lys Phe Lys Asp Lys Ala Thr Phe Thr Val Asp Lys
        835                 840                 845
Ser Ser Ser Thr Ala Tyr Met Glu Leu Leu Ser Leu Thr Ser Glu Asp
850                 855                 860
```

Ser Ala Val Tyr Tyr Cys Ala Arg Ser Gly Tyr Tyr Gly Asp Ser Asp
865                 870                 875                 880

Trp Tyr Phe Asp Val Trp Gly Ala Gly Thr Thr Val Thr Val Ser Ser
            885                 890                 895

<210> SEQ ID NO 2
<211> LENGTH: 896
<212> TYPE: PRT
<213> ORGANISM: Artificial Sequence
<220> FEATURE:
<223> OTHER INFORMATION: Synthetic recombinant toxin molecule

<400> SEQUENCE: 2

Ala Gly Ala Asp Asp Val Val Asp Ser Ser Lys Ser Phe Val Met Glu
1               5                   10                  15

Asn Phe Ala Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

```
Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
            370                 375                 380

His Lys Thr Gln Pro Phe Leu Pro Trp Asp Ile Gln Met Thr Gln Thr
385                 390                 395                 400

Thr Ser Ser Leu Ser Ala Ser Leu Gly Asp Arg Val Thr Ile Ser Cys
                405                 410                 415

Arg Ala Ser Gln Asp Ile Arg Asn Tyr Leu Asn Trp Tyr Gln Gln Lys
            420                 425                 430

Pro Asp Gly Thr Val Lys Leu Leu Ile Tyr Tyr Thr Ser Arg Leu His
            435                 440                 445

Ser Gly Val Pro Ser Lys Phe Ser Gly Ser Gly Ser Gly Thr Asp Tyr
            450                 455                 460

Ser Leu Thr Ile Ser Asn Leu Glu Gln Glu Asp Ile Ala Thr Tyr Phe
465                 470                 475                 480

Cys Gln Gln Gly Asn Thr Leu Pro Trp Thr Phe Ala Gly Gly Thr Lys
                485                 490                 495

Leu Glu Ile Lys Gly Gly Gly Gly Ser Gly Gly Gly Gly Ser Gly Gly
            500                 505                 510

Gly Gly Ser Glu Val Gln Leu Gln Gln Ser Gly Pro Glu Leu Val Lys
            515                 520                 525

Pro Gly Ala Ser Met Lys Ile Ser Cys Lys Ala Ser Gly Tyr Ser Phe
            530                 535                 540

Thr Gly Tyr Thr Met Asn Trp Val Lys Gln Ser His Gly Lys Asn Leu
545                 550                 555                 560

Glu Trp Met Gly Leu Ile Asn Pro Tyr Lys Gly Val Ser Thr Tyr Asn
                565                 570                 575

Gln Lys Phe Lys Asp Lys Ala Thr Leu Thr Val Asp Lys Ser Ser Ser
            580                 585                 590

Thr Ala Tyr Met Glu Leu Leu Ser Leu Thr Ser Glu Asp Ser Ala Val
            595                 600                 605

Tyr Tyr Cys Ala Arg Ser Gly Tyr Tyr Gly Asp Ser Asp Trp Tyr Phe
            610                 615                 620

Asp Val Trp Gly Ala Gly Thr Thr Val Thr Val Ser Ser Gly Gly Gly
625                 630                 635                 640

Gly Ser Gly Gly Gly Gly Ser Gly Gly Gly Gly Ser Asp Ile Gln Met
                645                 650                 655

Thr Gln Thr Thr Ser Ser Leu Ser Ala Ser Leu Gly Asp Arg Val Thr
            660                 665                 670

Ile Ser Cys Arg Ala Ser Gln Asp Ile Arg Asn Tyr Leu Asn Trp Tyr
            675                 680                 685

Gln Gln Lys Pro Asp Gly Thr Val Lys Leu Leu Ile Tyr Tyr Thr Ser
            690                 695                 700

Arg Leu His Ser Gly Val Pro Ser Lys Phe Ser Gly Ser Gly Ser Gly
705                 710                 715                 720

Thr Asp Tyr Ser Leu Thr Ile Ser Asn Leu Glu Gln Glu Asp Ile Ala
                725                 730                 735

Thr Tyr Phe Cys Gln Gln Gly Asn Thr Leu Pro Trp Thr Phe Ala Gly
            740                 745                 750
```

```
Gly Thr Lys Leu Glu Ile Lys Gly Gly Ser Gly Gly Gly
        755                 760             765

Ser Gly Gly Gly Ser Glu Val Gln Leu Gln Ser Gly Pro Glu
770                 775             780

Leu Val Lys Pro Gly Ala Ser Met Lys Ile Ser Cys Lys Ala Ser Gly
785             790              795                 800

Tyr Ser Phe Thr Gly Tyr Thr Met Asn Trp Val Lys Gln Ser His Gly
                805             810              815

Lys Asn Leu Glu Trp Met Gly Leu Ile Asn Pro Tyr Lys Gly Val Ser
            820             825             830

Thr Tyr Asn Gln Lys Phe Lys Asp Lys Ala Thr Leu Thr Val Asp Lys
        835             840              845

Ser Ser Ser Thr Ala Tyr Met Glu Leu Leu Ser Leu Thr Ser Glu Asp
850             855              860

Ser Ala Val Tyr Tyr Cys Ala Arg Ser Gly Tyr Tyr Gly Asp Ser Asp
865             870              875             880

Trp Tyr Phe Asp Val Trp Gly Gln Gly Thr Thr Leu Thr Val Phe Ser
                885             890              895
```

<210> SEQ ID NO 3  
<211> LENGTH: 895  
<212> TYPE: PRT  
<213> ORGANISM: Artificial Sequence  
<220> FEATURE:  
<223> OTHER INFORMATION: Synthetic recombinant toxin molecule

<400> SEQUENCE: 3

```
Gly Ala Asp Asp Val Val Asp Ser Ser Lys Ser Phe Val Met Glu Asn
1               5                   10                  15

Phe Ala Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220
```

```
Pro Ile Lys Asn Lys Met Ser Glu Ser Pro Ala Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
                260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Thr Ala Ala Leu
        290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
                340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
        370                 375                 380

Lys Thr Gln Pro Phe Leu Pro Trp Asp Ile Gln Met Thr Gln Thr Thr
385                 390                 395                 400

Ser Ser Leu Ser Ala Ser Leu Gly Asp Arg Val Thr Ile Ser Cys Arg
                405                 410                 415

Ala Ser Gln Asp Ile Arg Asn Tyr Leu Asn Trp Tyr Gln Gln Lys Pro
            420                 425                 430

Asp Gly Thr Val Lys Leu Leu Ile Tyr Tyr Thr Ser Arg Leu His Ser
        435                 440                 445

Gly Val Pro Ser Lys Phe Ser Gly Ser Gly Ser Gly Thr Asp Tyr Ser
450                 455                 460

Leu Thr Ile Ser Asn Leu Glu Gln Glu Asp Ile Ala Thr Tyr Phe Cys
465                 470                 475                 480

Gln Gln Gly Asn Thr Leu Pro Trp Thr Phe Ala Gly Gly Thr Lys Leu
                485                 490                 495

Glu Ile Lys Gly Gly Gly Ser Gly Gly Gly Ser Gly Gly Gly
            500                 505                 510

Gly Ser Glu Val Gln Leu Gln Gln Ser Gly Pro Glu Leu Val Lys Pro
        515                 520                 525

Gly Ala Ser Met Lys Ile Ser Cys Lys Ala Ser Gly Tyr Ser Phe Thr
530                 535                 540

Gly Tyr Thr Met Asn Trp Val Lys Gln Ser His Gly Lys Asn Leu Glu
545                 550                 555                 560

Trp Met Gly Leu Ile Asn Pro Tyr Lys Gly Val Ser Thr Tyr Asn Gln
                565                 570                 575

Lys Phe Lys Asp Lys Ala Thr Leu Thr Val Asp Lys Ser Ser Ser Thr
                580                 585                 590

Ala Tyr Met Glu Leu Leu Ser Leu Thr Ser Glu Asp Ser Ala Val Tyr
            595                 600                 605

Tyr Cys Ala Arg Ser Gly Tyr Tyr Gly Asp Ser Asp Trp Tyr Phe Asp
        610                 615                 620

Val Trp Gly Ala Gly Thr Thr Val Thr Val Ser Ser Gly Gly Gly Gly
625                 630                 635                 640
```

-continued

```
Ser Gly Gly Gly Ser Gly Gly Gly Ser Asp Ile Gln Met Thr
            645             650             655

Gln Thr Thr Ser Ser Leu Ser Ala Ser Leu Gly Asp Arg Val Thr Ile
            660             665             670

Ser Cys Arg Ala Ser Gln Asp Ile Arg Asn Tyr Leu Asn Trp Tyr Gln
            675             680             685

Gln Lys Pro Asp Gly Thr Val Lys Leu Leu Ile Tyr Tyr Thr Ser Arg
690             695             700

Leu His Ser Gly Val Pro Ser Lys Phe Ser Gly Ser Gly Ser Gly Thr
705             710             715             720

Asp Tyr Ser Leu Thr Ile Ser Asn Leu Glu Gln Glu Asp Ile Ala Thr
            725             730             735

Tyr Phe Cys Gln Gln Gly Asn Thr Leu Pro Trp Thr Phe Ala Gly Gly
            740             745             750

Thr Lys Leu Glu Ile Lys Gly Gly Gly Ser Gly Gly Gly Gly Ser
            755             760             765

Gly Gly Gly Ser Glu Val Gln Leu Gln Gln Ser Gly Pro Glu Leu
        770             775             780

Val Lys Pro Gly Ala Ser Met Lys Ile Ser Cys Lys Ala Ser Gly Tyr
785             790             795             800

Ser Phe Thr Gly Tyr Thr Met Asn Trp Val Lys Gln Ser His Gly Lys
            805             810             815

Asn Leu Glu Trp Met Gly Leu Ile Asn Pro Tyr Lys Gly Val Ser Thr
            820             825             830

Tyr Asn Gln Lys Phe Lys Asp Lys Ala Thr Leu Thr Val Asp Lys Ser
            835             840             845

Ser Ser Thr Ala Tyr Met Glu Leu Leu Ser Leu Thr Ser Glu Asp Ser
850             855             860

Ala Val Tyr Tyr Cys Ala Arg Ser Gly Tyr Tyr Gly Asp Ser Asp Trp
865             870             875             880

Tyr Phe Asp Val Trp Gly Gln Gly Thr Thr Leu Thr Val Phe Ser
            885             890             895
```

IMMUNOMODULATION BY ANTI-CD3 IMMUNOTOXINS TO TREAT CANCERS BEARING OR NOT UNIFORMLY BEARING SURFACE CD3

BACKGROUND OF THE INVENTION

Field of the Invention

The invention generally relates to methods of treating patients suffering from cancers that do not bear, or do not uniformly bear, or bear surface CD3 epitopes. In particular, the methods involve administering anti-CD3 immunotoxins to modulate the immune systems of such patients and achieve long-term immune protection against CD3 and non-CD3 cancers.

Background of the Invention

Two important tools in the treatment of cancer are immunotoxins and immunomodulatory agents. Immunotoxins are anti-human recombinant fusion proteins that target and kill specific types of cancer cells. Targeting is typically mediated via a targeting portion of the protein (e.g. a modified antibody or antibody fragment specific for binding to a particular epitope of interest), and killing is typically carried out by a toxin moiety that is attached to the targeting portion. Upon administration, immunotoxins thus directly target and bind to cancer cells that display the epitope of interest, and the toxic portion of the molecule then kills the cell to which it is bound. Destruction of cancer cells by immunotoxins thus occurs within the relatively short time frame during which they are in circulation, e.g. within hours or days of administration.

In contrast, immunomodulatory agents have a completely different mode of action. Rather than killing cancer cells outright, they work by "resetting" the immune system so that it recognizes and destroys cancer cells on its own. In cases of full-blown cancer, an individual's immune system has not been able to destroy cancer cells, possibly because they arise from pre-existing cells of the body and are thus recognized as innocuous "self" cells rather than as potentially dangerous "foreign" invaders. Immunomodulatory agents work by altering existing immune cells, thereby providing an opportunity for immune cell replication and the development of new lineages of immune cells that do recognize the cancer cells as "foreign". In other words, the body's immune tolerance of the cancer antigens is broken by the immunomodulatory agent. As a result of this mode of action, treatment with immunomodulatory agents displays tumor regression kinetics that differ from those of immunotoxins. The effects are usually delayed and can take a few months or even years to achieve their maximum levels. During this time, the immune system reconstitutes itself and, if conditions are right, is "retrained" to recognize cancer cells as foreign and mount an immune response against the cancer if it recurs. After treatment with an immunomodulatory agent, the course of tumor regression may not be linear but rather punctuated by the development of new tumors followed by regression as the body's immune system recognizes and then mounts a response to the tumor.

Ideally, for some cancer treatment protocols, a "short-acting" anti-cancer agent is used in conjunction with a "long-acting" immunomodulatory agent, the former resulting in an immediate killing of cancer cells, and the latter eliciting long-term anti-cancer protection. Some agents of both types are known and have been used with success. However, given the many types of cancers, the complexity of the disease, and the limited and variable efficacies of existing agents, this strategy is not always successful, and there remains an ongoing need to identify new anti-cancer agents and/or a need for new ways of using existing agents. In addition, currently known immunomodulatory agents typically have adverse side effects such as the development of autoimmune diseases. This likely results from the breaking of tolerance to self antigens during repopulation, which, in addition to the cancer cells, the immune system then "sees" as abnormal.

It would be a boon to have available additional immunomodulatory agents which can be used to stimulate the body's own cancer fighting abilities as described above, in particular with respect to preventing or treating recurrences or metastasis of the cancer over time. Further, the discovery of immunomodulatory agents that do not cause autoimmune disease in patients would be highly desirable.

U.S. Pat. Nos. 7,696,338 and 8,217,158 (Neville, Jr., et al.), the complete contents of which are herein incorporated by reference, describe methods of treating autoimmune diseases and CD3 bearing T cell leukemia or lymphoma using an antibody-DT mutant immunotoxin which routes by the anti-CD3 pathway. However, these patents do not describe the use of these immunotoxins as immunomodulatory agents.

SUMMARY OF THE INVENTION

The invention provides a new use for the anti-CD3 immunotoxins described in U.S. Pat. No. 7,696,338 and 8,217,158. The immunotoxins comprise antigen-binding domains of an anti-CD3 antibody and a portion of the diphtheria toxin protein. An exemplary immunotoxin of this type has been successfully used in clinical trials to treat CD3 bearing (i.e. T-cell) lymphomas and leukemias. In these cases, the rationale for administering the immunotoxin was to target and destroy extant cancer cells which bear CD3 epitopes, thereby providing a short-term, front line defense against the disease.

However, it has now been surprisingly discovered that the immunotoxin may effectively be used as an immunomodulating agent and can thus be used to provide long-term, far-reaching anti-cancer effects that are not related to (are separate or apart from) their immunotoxin activity. Without being bound by theory, it is believed that when administered, these agents attack and kill normal immune cells which bear CD3 epitopes (e.g. T cells), thereby depleting the immune cell population. The depletion is transient or temporary, and is followed by repopulation with new, peripheral T cells (homeostatic repopulation) which are susceptible to retraining. When exposed to cancer cell antigens, the new cadre of immune cells learns to recognize the antigens, and hence the cancer cells, as abnormal, to distinguish them from innocuous "self" or otherwise healthy tissue. In other words, use of these agents results in resetting or retraining of the immune system of the patient, and provides the patient with the ability to "naturally" fight the disease using his/her own immune defense system when cancer cells are later encountered. The discovery of this heretofore unrealized property of these immunotoxin molecules has resulted in the development of methods of treating cancers other than those of T-cell origin, i.e. methods for destroying or killing cancer cells which do not bear, or do not uniformly bear, CD3 epitopes. In particular, the agents are used to modulate a patient's immune system to recognize cancer cells as abnormal and to destroy them if/when they arise metastatically or during and after recurrence of the disease. Significantly, and in contrast to other immunomodulatory agents, the immunotoxins of the invention break immune tolerance of the tumor without breaking immune tolerance to self antigens and causing autoimmune diseases.

It is an object of this invention to provide methods of providing immunomodulation to a patient suffering from a cancer which does not bear, or does not uniformly bear, surface CD3 epitopes. The method comprises 1) administering to the patient an anti-CD3 specific immunotoxin in an amount sufficient to deplete extant T-cells of said patient; and 2) allowing repopulation and maturation of new T cells in said patient in the presence of said non-CD3 cancer cell antigens. In some aspects, the non-CD3 cancer cell antigens are released into circulation as a result of administering an antigen releasing anti-cancer therapy, for example, radiation therapy. In other aspects, the step of administering does not break immune tolerance to self antigens in said patient. The methods may further comprise a step of providing the non-CD3 cancer cell antigens to a patient to boost an immune response of the patient to the non-CD3 cancer cell antigens, at a period of time after the step of allowing. The step of providing may be performed after a recurrence of the cancer. In some aspects of the invention, the anti-CD3 specific immunotoxin is A-dmDT390-bisFv (UCHT1).

The invention also provides methods of lengthening survival time of a patient suffering from a cancer which does not bear, or does not uniformly bear, surface CD3 epitopes. The methods comprise 1) administering to the patient an anti-CD3 specific immunotoxin in an amount sufficient to deplete extant T-cells of the patient; and allowing repopulation and maturation of new T cells in the patient in the presence of the non-CD3 cancer cell antigens.

The invention also provides methods of preparing the immune system of a patient to recognize and kill metastatic and/or recurrent cancer, wherein the patient is suffering from a cancer which does not bear, or does not uniformly bear, surface CD3 epitopes. The methods comprise 1) administering to the patient an anti-CD3 specific immunotoxin in an amount sufficient to deplete extant T-cells of the patient; and allowing repopulation and maturation of new T cells in the patient in the presence of the non-CD3 cancer cell antigens.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

FIG. 2. Amino acid sequence of A-dmDT390-bisFv (UCHT1) (SEQ ID NO: 1).

FIGS. 3A and B. Amino acid sequences of exemplary fusion proteins that may be used in the practice of the invention (SEQ ID NOS: 2 and 3).

DETAILED DESCRIPTION

Figure 1:
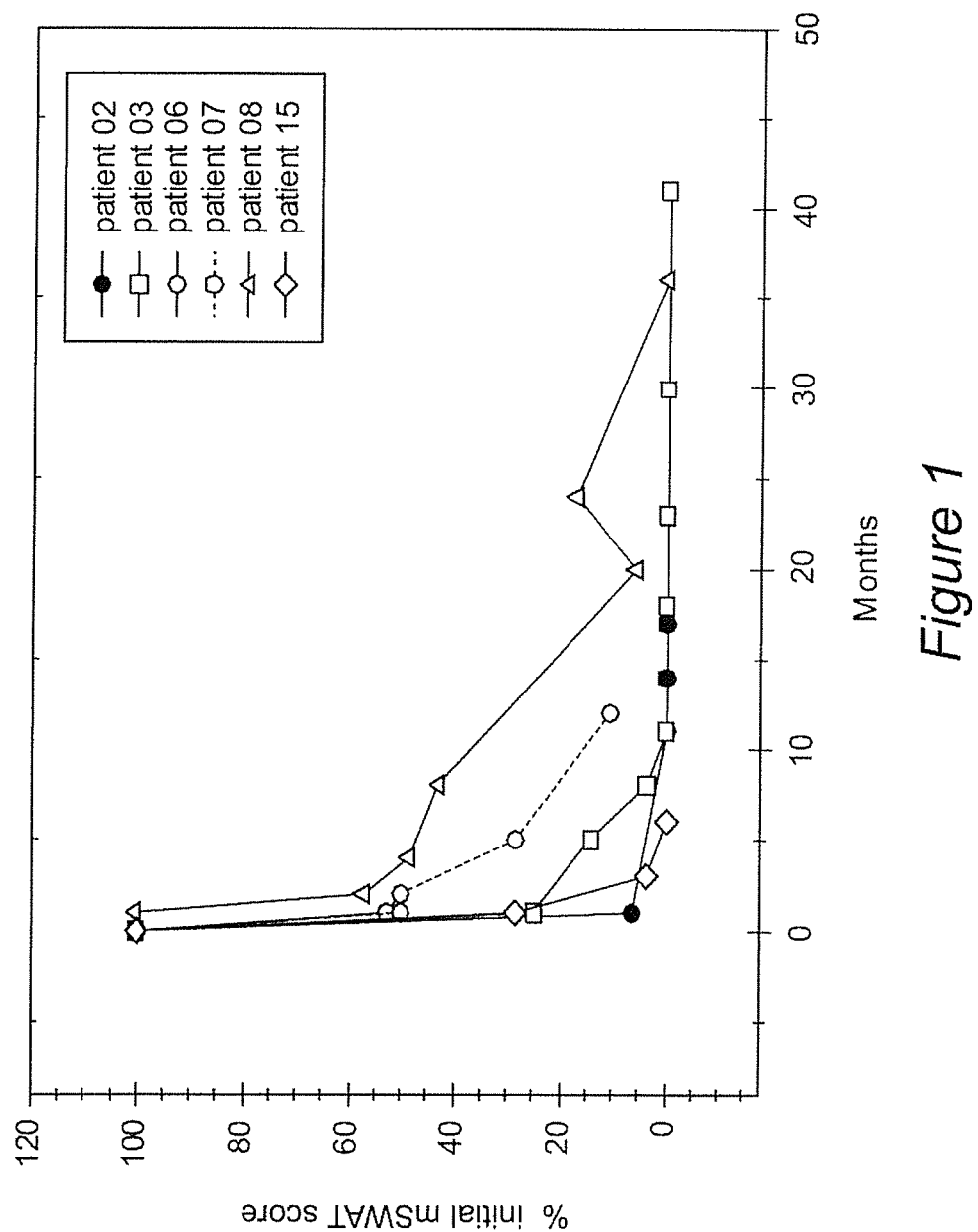
FIG. 1. % of the initial Modified Severity Weighted Assessment Tool (mSWAT) score versus time after a 4-day treatment period. The mSWAT score represents the skin tumor burden and is measured by determining the % surface area of skin involved times a multiplier that is 1 for patch, 2 for plaque and 4 for tumor.

The present invention provides a new use for the immunotoxin molecules described in U.S. Pat. Nos. 7,696,338 and 8,217,158 to Neville, the complete contents of both of which are hereby incorporated by reference in entirety. The new uses include administration of the molecules to bring about immunomodulation in patients with cancers that do not bear, or do not uniformly bear, CD3 antigens. Prior to the present invention, these agents were not administered to such patients because these agents were designed as anti-CD3 toxins and the subject cancers do not bear, or do not uniformly bear, CD3 antigens.

U.S. Pat. Nos. 7,696,338 and 8,217,158 describe various embodiments of these immunotoxins in detail. The immunotoxins are chimeras or fusion proteins which comprise a recombinant toxin moiety linked to an antibody moiety that is specific for binding to CD3 epitopes. The antibody moiety is responsible for binding the immunotoxin to the CD3εγ subunit of the T cell receptor complex, enabling the molecule to specifically target and bind to T-cells bearing the CD3 receptor. Once bound, the toxin moiety of the molecule enters and kills the cells. In some embodiments, the toxin moiety is, for example, a truncated diphtheria toxin (DT) moiety or *pseudomonas* exotoxin A (ETA) toxin moiety, and the antibody moiety comprises two single chain Fvs of and anti-CD3 antibody. The amino acid sequence of several exemplary immunotoxins that may be used in the practice of the invention are shown in FIGS. 2-3 and SEQ ID NOS: 1-3. In particular, the amino acid sequence of A-dmDT390-bisFv (UCHT1) is shown in FIG. 2 and set forth in SEQ ID NO: 1. Variants of these sequences may also be employed, e.g. variants with conservatively substituted amino acid sequences, proteolytic fragments, variants that do and do not include an amino terminal Met residue, codon optimized and/or humanized variants, etc. In addition, serine protease cleavage at e.g. furin cleavage site RVRR:SVGS (see residues 191-198 of SEQ ID NO: 1) or at other sites may occur, without disrupting the disulfide bridge between cysteines 188 and 202 Any such variant may be utilized to treat or prevent cancer as described herein, so long as immunotoxic activity is retained in the variant. Suitable nucleic acid molecules for encoding the immunotoxins include any that produce the indicated proteins when transcribed/translated (e.g. RNA, DNA, etc.) including genes and/or recombinant genes whether isolated, present in a vector, or present in a cell.

The methods take advantage of the sophisticated defense mechanisms of jawed vertebrates, including humans, i.e. the ability to adapt over time to recognize specific pathogens more efficiently. This adaptive (or acquired) immunity creates immunological memory after an initial response to antigens of a specific pathogen (or in this case, cancer cell antigens) leading to an enhanced response to subsequent encounters with the same antigens. (This process of acquired immunity is the also basis of vaccination.) The methods involve identifying a patient in need of immunomodulation and administering an immunotoxin as described herein, for the purpose of transiently or temporarily depleting the patient's T cells. The method is carried out under conditions in which, when natural repopulation of the T cells ensues, the new T cells are exposed to circulating cancer cell antigens. Exposure to cancer cell antigens during repopulation results in a sensitization of the new T cell population to the antigens, and the development of immunological memory so that, upon subsequent encounters with the same cancer antigens, they are recognized by the immune system and attacked and killed. Therefore, metastatic and/or recurrent tumors that develop later are eventually resolved (destroyed) by the body's own immune system, with or without further anti-cancer treatment. In some embodiments, described in detail below, the methods further include a step or steps of priming the immune system by additional exposures of the immune system to the cancer antigens, e.g. by releasing antigens into the circulatory system via radiation of metastatic or recurring tumors. The use of the methods thus facilitates the treatment of metastatic and/or recurring cancer ahead of time (i.e. prior to the metastasis or recurrence) by augmenting the patient's natural ability to conduct immune surveillance on an ongoing basis and fight the development of tumors. Practice of the methods lengthens the survival time of cancer patients, and prevents and/or aids in the eradication of metastatic or recurring tumors and cancerous lesions.

In one aspect of the invention, subjects who are identified as suitable for treatment using the methods of the invention are those who are diagnosed as suffering from a cancer in which the cancer cells do not bear surface CD3 epitopes i.e. CD3 epitopes are not present on (are absent from) the surface of the cancer cells. Determination of the phenotype of cancer cells with respect to the presence or absence of a particular epitope (e.g. CD3) is well known in the art. For example, samples of tumor cells are obtained and the nature (type, identity, etc.) of the antigens that are displayed is determined or confirmed using immunochemistry, e.g. by exposing the sample to antibodies specific for one or more antigens of interest (e.g. CD3) and measuring the extent of binding, if any, of the antibodies to the cancer cells using standard technologies, e.g. ELISA reactions, flow cytometry, etc. Cancer which do not bear surface CD3 epitopes include any non-T cell leukemia or lymphoma (i.e. any cancer that is not a T cell leukemia or lymphoma) such as, but are not limited to: some cases of acute lymphoblastic leukemia (ALL) e.g. those in which the cancer cells do not uniformly bear CD3 epitopes; acute myeloid leukemia (AML); adrenocortical carcinoma; atypical teratoid/rhabdoid tumors; central nervous system cancers; basal cell carcinoma (e.g. nonmelanoma); bile duct cancer; extrahepatic bladder cancer; bone cancers (e.g. Ewing sarcoma family of tumors, osteosarcoma and malignant fibrous histiocytoma; brain stem glioma; brain tumors (e.g. astrocytomas, brain and spinal cord tumors, CNS atypical teratoid/rhabdoid tumor, CNS embryonal tumors, CNS germ cell tumors, etc.); craniopharyngioma, ependymom; breast cancer; bronchial tumors, Burkitt lymphoma gastrointestinal tumors; cardiac (heart) tumors; cervical cancer; chordoma; chronic lymphocytic leukemia (CLL); chronic myelogenous leukemia (CML); chronic myeloproliferative disorder; colon cancer; colorectal cancer; craniopharyngioma, cutaneous T-Cell lymphoma; extrahepatic bile duct tumors; ductal carcinoma in situ (DCIS); embryonal tumors; endometrial cancer; esophageal cancer; esthesioneuroblastoma; Ewing sarcoma; extracranial germ cell tumor; extragonadal germ cell tumor; eye cancers (intraocular melanoma, retinoblastoma); fibrous histiocytoma of bone; osteosarcoma; gallbladder cancer; gastric (stomach) cancer; gastrointestinal carcinoid tumor; gastrointestinal stromal tumors (GIST); gestational trophoblastic tumor; glioma; hairy cell leukemia; head and neck cancer; heart cancer; hepatocellular (liver) cancer; hypopharyngeal cancer; intraocular melanoma; islet cell tumors; pancreatic neuroendocrine tumors; kidney (e.g. renal cell and Wilms tumor); Langerhans cell histiocytosis; laryngeal cancer; leukemia; liver cancer (primary); lobular carcinoma in situ (LCIS); lung cancer (non-small cell, small cell); lymphomas; Waldenström macroglobulinemia; male breast cancer; malignant mesothelioma, metastatic squamous neck cancer with occult primary midline tract carcinoma involving NUT gene; mouth cancer; multiple endocrine neoplasia syndromes; myelodysplastic syndromes; myelodysplastic/myeloproliferative neoplasms; Chronic Myelogenous Leukemia (CML); Acute Myeloid Leukemia (AML); multiple myeloma; chronic myeloproliferative disorders; nasal cavity and paranasal sinus cancer; nasopharyngeal cancer; neuroblastoma; non-Hodgkin lymphoma; oral cancer; oral cavity cancer; lip and oropharyngeal cancer; osteosarcoma and malignant fibrous histiocytoma of bone; ovarian cancer; pancreatic cancer; pancreatic neuroendocrine tumors (Islet Cell tumors); papillomatosis; paraganglioma; parathyroid cancer; penile cancer; pharyngeal cancer; neochromocytoma; pituitary tumor; plasma cell neoplasm/multiple myeloma; pleuropulmonary blastoma; CNS lymphoma; prostate cancer; rectal cancer; renal cell (kidney) cancer; salivary gland cancer; sarcomas (Ewing, Kaposi, osteosarcoma, rhabdomyosarcoma, soft tissue, uterine); skin cancers (melanoma, Merkel cell carcinoma, nonmelanoma); small cell lung cancer; small intestine cancer; squamous cell carcinoma; squamous neck cancer with occult primary, metastatic stomach (gastric) cancer; testicular cancer; throat cancer; thymoma and thymic carcinoma; thyroid cancer; transitional cell cancer of the renal pelvis and ureter; trophoblastic tumor, gestational; urethral cancer; uterine cancer, endometrial cancer; uterine sarcoma; vaginal cancer; vulvar cancer; Waldenström macroglobulinemia; Wilms tumor; nasal cavity and paranasal sinus cancer; nasopharyngeal cancer; neuroblastoma; non-small cell lung cancer; and metastases and recurrences thereof.

In other aspects of the invention, the patients suffering from cancers that do not uniformly bear surface CD3 epitopes, i.e. CD3 epitopes may be present on some but not all of the cancer cells of the tumor, may be treated with the immunotoxin A-dmDT390-bisFv(UCHT1). For example, in T-ALL, many patients have tumor blast cells do not display surface CD3 but there are also many patients whose blasts display between 10% and 80% CD3. The present method is beneficial for the treatment of such cancers because, even though administering a CD3 toxic agent would kill the portion of the cells that do display CD3, cancer cells that do not display CD3 would not be destroyed. In this aspect, administration of the immunotoxins described herein will kill those cancer cells that do display CD3 during the short time frame when the immunotoxins are in circulation. However, the non-CD3 portion of the cells are not killed outright by the immunotoxin (although they may be destroyed by administration of another agent), but will be subject to attack by the patient's immune system after depletion/repopulation as described herein.

The present invention involves administering the immunotoxic agents described herein to patients in a therapeutically beneficial quantity, e.g. a quantity that results is depletion of the T cell population of the patient to a level that is sufficient to elicit repopulation of the immune system. Depletion of the T cell population refers to the destruction or killing of at least about 90 to 99% or more (e.g. 100%) of the T cells present in the subject, but in some cases killing of about 50% or more (e.g. 55, 60, 65, 70, 75 80 or 85%) may suffice.

The methods of the invention are carried out by administering compositions which include the fusion proteins described herein, or nucleic acid sequences encoding them, and a pharmacologically suitable (physiologically compatible) carrier. The compositions are also encompassed by the invention. The preparation of such compositions is well known to those of skill in the art. Typically, such compositions are prepared either as liquid solutions or suspensions. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like.

Subjects treated by the methods of the invention are generally mammals, and frequently humans. However, the invention also encompasses veterinary applications e.g. the treatment of animals, especially companion pets, prize livestock, etc.

Those of skill in the art are familiar with the administration of chemotherapeutic agents, and the compositions (preparations) may be administered by any of the many suitable means which are well known, including but not limited to: by injection, inhalation, orally, intravaginally, intranasally, topically, as eye drops, via sprays, etc. Generally, the mode of administration is intravenous or topical. In addition, the compositions may be administered in conjunction with other treatment modalities such as substances that boost the immune system, various other chemotherapeutic agents, pain medication, anti-nausea medication, anti-allergy agents (e.g. anti-histamines), and the like.

The immunotoxins described herein may be administered as immunomodulating agents at any desired time after diagnosis of a cancer, and by any suitable protocol or schedule. They may be administered before, after or at the same time as other anticancer agents. For example, they may be administered prior to the commencement of treatment with other cytotoxic agents or therapies, and/or together with them, or after other cytotoxic agents have been administered, e.g. several days or weeks afterwards. If administered "together" with another anti-cancer agent, they may be provided in separate compositions that are administered within a short time of each other, e.g. within minutes, hours or days, or using a single composition that contains at least one (i.e. one or more) immunotoxin and one or more than one other anti-cancer agent, etc.

The amount of agent that is administered may vary according to parameters that are understood by those of skill in the art, e.g. by a skilled medical practitioner. Recommended doses and particular protocols for administration may be established during clinical trials. The amount may vary based on e.g. the body weight, gender, age, overall condition, etc. of the patient, and/or on the type and stage of disease, and whether or not other therapeutic agents are being administered, etc. Generally, the total amount administered during a round of chemotherapy (scheduled to take place over e.g. a period of 5 days) will range from about 10 to about 60 µg/kg of body weight, e.g. the amount that is administered may be, for example, about 10, 15, 20, 25, 30, 35, 40, 45, 50, 55 or 60 µg/kg of body weight. Typically, about 20 µg/kg of body weight is administered. This amount is usually administered at multiple times or sessions during a single day of e.g. 1-2 µg/kg of body weight per session, with e.g. 1-6 sessions per day, and usually about 2 sessions per day. The number of weeks for which the treatment proceeds may also vary, depending on the factors which impact dosage listed above. Generally, 1 week of treatment is carried out, although the number of weeks can be 1, 2, 3, 4, 5, 6, or more, as deemed beneficial for the patient. When practiced in conjunction with radiation therapy, a course of treatment typically last for about 1 week. A course of treatment may be repeated as needed throughout the patient's lifetime, especially if there is a recurrence of the cancer. However, for such repetitions of treatment, in general it is not necessary to repeat the anti-CD3 immunomodulator, only the local tumor radiation.

Since the fusion proteins of the invention are used as immunomodulators rather than as immunotoxins, other toxic agents and/or other therapies may be used to kill the cancer cells outright, to cause tumor shrinkage, etc. In fact, the CD3 specific immunotoxins described herein would not be effective if used for such short-term, front line therapy since they are specific only for CD3 bearing tumors. Thus, one or more other anti-cancer agents or anti-cancer modalities or therapies are also generally administered, examples of which include but are not limited to: cytotoxic immunotoxins targeting the specific tumor or blood vessels growing into the tumor, cytotoxic antineoplastic drugs such as alkylating agents cisplatin, carboplatin, oroxaliplatin; anti-metabolites which masquerade as purines (e.g. azathioprine, mercaptopurine) or pyrimidines; plant alkaloids and terpenoids, e.g. vinca alkaloids such as vincristine, vinblastine, vinorelbine, vindesine; podophyllotoxin, etoposide and teniposide; taxanes such as paclitaxel; type I topoisomerase inhibitors including the camptothecins irinotecan and topotecan, and type II topoisomerase inhibitors such as amsacrine, etoposide, etoposide phosphate, and teniposide; and cytotoxic antibiotics such as actinomycin, anthracyclines, doxorubicin, daunorubicin, valrubicin idarubicin, epirubicin, bleomycin, plicamycin and mitomycin; gene therapy (e.g. to deliver a nucleic acid encoding an anti-cancer agent to a tumor), surgery/resection of tumors; hormonal therapy; administration of angiogenesis inhibitors; administration of other immunomodulating agents or therapies (e.g. allogeneic or autologous hematopoietic stem cell transplantation; by radiation therapy via external beam radiotherapy (EBRT) or internally via brachytherapy, electrochemotherapy; untraviolet (UV) light therapy; etc.

In some aspects, initial killing of cancer cells and the resulting release of cancer antigens into the circulation is carried out by local radiation of one or more cancerous lesions, which may be metastatic lesions, e.g. using Stereotactic Body Radiation Therapy (SBRT) techniques. In this case, the amount of radiation that is delivered is typically in the range of from about the typical dose for a solid epithelial tumor ranges from 60 to 80 Gy in total, while lymphomas are treated with 20 to 40 Gy. Preventative (adjuvant) doses are typically around 45-60 Gy (for breast, head, and neck cancers.) Generally, a patient receives about 1.8-2 Gy fractions per exposure. Many factors are considered when selecting a dose, including whether the patient is receiving chemotherapy, patient co-morbidities, whether radiation therapy is being administered before or after surgery, and the degree of success of surgery, etc. There is some evidence that higher doses of radiation (e.g. in the range of 10-20 Gy per exposure) may increase the response rate of lesions outside of the radiation field and thus provide a more marked effect with respect to immunomodulation.

Cancer treatment, including immunomodulation, is generally begun as soon after diagnosis as possible. This is especially advantageous for immunomodulation because the benefits of the treatment are typically not observed for at least weeks, usually months, or even years after the treatment, and it is desirable for the benefits to accrue as soon as possible. Administration is generally coordinated with other therapies that release cancer antigens to provide an opportunity for repopulating T cells to be "trained". Therefore, the present methods may also include a step of killing tumor cells in a manner that releases tumor antigens, to facilitate the development of immune cell memory with respect to cancer antigens.

The step of killing cancer cells to release antigen is generally carried out early in treatment, and may be sufficient to put the immune system in condition to monitor, recognize and eradicate new tumors shortly after recurrence without further treatment. However, in other aspects, antigen-releasing therapy may be reapplied later during the course of treatment in order to further boost the immune response, analogous to a vaccination protocol. This may be readily accomplished if the cancer recurs since a treatment that releases antigen can be administered at that time. However, if no visible or detectable recurrence is present, it may be possible to effect boosting by administering tumor cells or antigen-bearing fragments thereof from the original tumors that have been preserved for the purpose. In this case, the cells or fragments can be administered e.g. 3-6 months after the initial treatment as a "booster", and/or at longer intervals (e.g. yearly) thereafter, if desired.

The examples presented below are intended to illustrate various exemplary aspects of the invention but should not be interpreted so as to limit the invention in any way.

EXAMPLES

Example 1. Treatment of Cutaneous T Cell Lymphoma with A-dmDT390-bisFv(UCHT1)

A number of immunomodulators have been used to treat solid cancers such as renal cell cancer and melanoma. Among these are infusions of IL-2 and antibodies directed at the activating lymphocyte epitopes CTLA-4 and the inhibitory lymphocyte epitope PD1 as well as its ligand PD1-L. The response rates for anti-CTLA-4, ipilimumab, have been low, around 10-15%. Immunomodulators such as anti-CTLA-4 or IL-2 may have a higher response rate on solid tumors when combined with local radiation therapy of metastatic lesions, likely by increasing the pool of presentable tumor antigen (abscopal effect).

An unfortunate side effect of the immunomodulators IL-2, anti-CTLA-4, anti-PD1 and anti-PD1-L is an increased incidence of autoimmune diseases, presumably because of enhanced T cell activity that breaks tolerance toward self antigens.

A-dmDT390-bisFv (UCHT1), an anti-T cell immunotoxin, is being studied as a treatment for cutaneous T cell lymphoma and other CD3+ malignant diseases. Eighteen patients with CD3+ lymphoma were treated to date in the phase I dose escalation portion of the trial. Fifteen patients received the full course of 8 infusions over 4 days, 4-6 hours apart. The total dose ranged between 20 and 90 µg/kg and 60 µg/kg was determined to be the maximum tolerable dose. 6 patients were treated in a 20 µg/kg dose cohort. Three showed partial responses of skin lesions with the first month. Two of these went on to complete responses at 11 months post treatment. Most of the treated patients (15) showed a 2 log or greater transient depletion of circulating T cells with a repopulation of these cells, except for the naïve CD4 subset, at 20 days.

The results for the resounding patients are presented in FIG. 1. As can be see, the kinetics of decrease in mSWAT exhibits a rapid phase of about 2 months and a slower phase between 3-24 months. As can also be seen, four out of six partial responses of patients converted to complete responses at times ranging between 6 and 24 months following the completion of the 4-day treatment protocol, and no other treatment took place except for patient #2 who received narrow band UV-B after a complete remission and a subsequent relapse. These data are consistent with A-dmDT390-bisFv (UCHT1) acting as an immunomodulator. For these particular patients, it is likely that the anti-T cell immunotoxin has two distinct effects in treating T cell lymphoma: i) it kills malignant T cells thus releasing tumor antigens; and ii) it also functions as an immunomodulator via the depletion of normal T cells and subsequent repopulation that breaks tumor antigen tolerance during homeostatic T cell proliferation or modification of Tregs. Significantly, in contrast to patients treated with other immunomodulators, patients receiving A-dmDT390-bisFv (UCHT1) did not develop autoimmune diseases.

Example 2. Phase I/II Study of A-dmDT390-bisFv (UCHT1) Fusion Protein in Patients with Surface CD3+ Malignant T Cell Disease: Summary of Patients #2 & 7

Patient #2 is an 82-year-old Caucasian male who developed cutaneous T cell lymphoma (CTCL) with a maculopapular rash on his buttocks and a groin mass. Biopsy of both lesions showed lymphoblastoid T-cell lymphoma. A computed tomography (CT) scan showed diffuse adenopathy. He received six cycles of CHOP chemotherapy (i.e., cyclophosphamide, doxorubicin, vincristine, and methylprednisolone), but after several years the rash recurred. Biopsy again showed CTCL. He did not have node or marrow involvement based on CT scans and bone marrow biopsies and was staged as IB. He was treated with A-dmDT390-bisFv(UCHT1) and achieved a response lasting 17 months, which included partial remission (PR) of 11 months duration and complete remission (CR) of 6 months duration. Patient #2 was then removed from the study due to return of buttock lesions that responded to narrow band UVB. 2.5 years later, he was reenrolled in the study to follow his progress. He has been in complete remission since the UVB treatment. The total duration since treatment with A-dmDT390-bisFv(UCHT1) is 4.4 yrs.

Comment:

Administration of the anti-CD3 immunotoxin A-dmDT390-bisFv(UCHT1) was expected to kill a large fraction of tumor cells but was not expected to provide lasting therapeutic value. However, the course of the disease for patient #2 surprisingly showed partial remission, complete remission, relapse and then complete remission for the 4.4. years after administration during which he was followed. Surprisingly, the duration of the effect of administration of A-dmDT390-bisFv(UCHT1) outlasted even the relapse that occurred after administration of CHOP chemotherapy. This "up-and-down" disease course is typical of what is seen when cancers are treated with immunomodulators, and indicates that the anti-CD3 immunotoxin A-dmDT390-bisFv(UCHT1) functioned as an immunomodulator in this patient.

Patient #7 is a 43-year-old Afro-American male who was diagnosed with mycosis fungoides (CTCL). He received narrow range UVB and clobetasol and his disease was staged as IIB. He had plaques, patches and tumors and an mSWAT of 14. He received 5.0 µg/kg/dose twice a day for 4 days of A-dmDT390-bisFv(UCHT1) and had a PR lasting 14 months, with mSWAT dropping to 1.5. At 15 months he developed two new tumors in his flank. He was placed on Bexarotene and then received local radiation to these tumors. Two years later this patient reports that his most recent tumors regressed and that he has no skin lesions.

Comment:

This patient is likely to be in complete remission at present. After a marked improvement he suffered a relapse that responded to local radiation. What is unusual is that he has remained free of skin lesions and tumors for the last two years off all therapy. This indicates that the anti-CD3 immunotoxin A-dmDT390-bisFv(UCHT1) also functioned as a long lasting immunomodulator in this patient. Further, the immunomodulation activity may have been augmented by tumor antigen priming accomplished by local radiation of the flank tumors. The radiation treatment served to i) keep new tumor growth in check, and ii) release antigen into the bloodstream to prime or "boost" the immune response.

Example 3. Use of A-dmDT390-bisFv (UCHT1) as an Immunomodulator

Based on the results obtained in Examples 1 and 2, A-dmDT390-bisFv (UCHT1) is administered as an immunomodulator of late stage metastatic melanoma or renal cell cancer in combination with palliative radiation to induce the priming of activated T cells by releasing tumor antigens. The safety of combining the immunotixin with palliative radiation therapy in patients with stage IV melanoma or renal cell cancer is determined. The tumor response and duration of response at non-irradiated sites (abscopal effect) is documented. T cell activation occurring after administration of A-dmDT390-bisFv(UCHT1) and local radiation to a metastatic lesion of melanoma or renal cell cancer is assessed by following CD4$^+$ T cells for HLA-DR and ICOS$^{high}$ T cells using flow cytometry.

20 µg/kg dose (see Example 1) is chosen for immunomodulation. The A-dmDT390-bisFv (UCHT1) dose of 20 µg/kg total is given as 2.5 µg/kg/injection twice a day at 4-6 hours intervals for four consecutive days (days 1-4) into a free flowing IV over a period of approximately 15 minutes. This is ⅓ the MTD found in the phase I portion of the clinical trial treating T cell lymphomas (see Example 1) and ¹⁄₁₀ the MTD found in preclinical studies with mice, rats and squirrel monkeys. The doses on day 2, 3, and 4 are given only in the absence of grade 3 non-hematologic toxicity.

Patients are admitted to the hospital on day 0 for the first two infusions on day 1. Infusions for days 2, 3 and 4 and fractionated radiation are done in the clinic on an outpatient basis. Prior to each of the eight infusions of drug, the patients receive premedication with diphenhydramine (50 mg PO), ranitidine (150 mg PO) and acetaminophen (650 mg). If indicated, an optional premedication of intravenous (IV) corticosteroids (e.g. 50-100 mg hydrocortisone) or oral prednisone is given. The patients also receive 1 liter 5% dextrose/0.45% NaCl IV daily for four days treatment. Prophylactic antibiotics are given for two weeks: acyclovir (400 mg PO) twice a day; Bactrim DS (SMZ-TMP DS 800-160 mg, 1 tablet PO three times a week e.g. Monday, Wednesday and Friday). Patients are also monitored with cytomegalovirus (CMV) and Epstein Barr virus (EBV) PCR tests. EBV PCR is performed at screening, day 5, day 10, and day 23. CMV PCR is performed at screening, day 10, day 23, and day 37. Dose Limiting Toxicity (DLT) is defined as a drug-related non-hematologic toxicity of grade 3 severity or greater except for transient (≤7 days) grade 4 asymptomatic elevations of transaminases or creatine phosphokinase (CPK) and transient (28 days) grade 3 and 4 lymphopenias. Lymphopenia is not considered a DLT since it is the pharmacologic property of the study drug. Grade 3 reactivation of EBV and CMV are not considered DLTs since they are often associated with lymphopenia. EBV and CMV reactivations higher than grade 3 are considered DLTs. Patients receive fractionated palliative radiation on days 1, 3 and 5 (in between the two infusions on days 1 and 3). The radiation dose is determined by the radiologist on a per patient basis depending on the size and position of the metastatic lesion receiving RT. Vital signs including blood pressure, pulse, temperature, respirations are monitored and patients are retained in or eliminated from the study according to established criteria for safety.

Treatment of the patients with A-dmDT390-bisFv (UCHT1) results in T cell transient depletion followed by T-cell repopulation and activation, and in the breaking of tumor tolerance. The outcome is partial and/or full remission. In some cases, punctuated remission is observed, with periods of partial remission interspersed with periods of recurrence and periods of full remission, even in the absence of administration of additional cytotoxic agents. In some cases, recurrent tumors are treated with radiation to release tumor antigens to further prime or sensitize the immune system to the tumor antigens. The protective effects of A-dmDT390-bisFv (UCHT1) are long-lasting, enduring for months and even several years after initial administration.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A method of treating a patient with cutaneous T cell lymphoma (CTCL), wherein the patient is not an allogenic or autologous transplant patient, comprising:
    administering to the patient an anti-CD3 specific immunotoxin in an amount sufficient to
        i) kill at least a portion of CTCL cancer cells, thereby releasing CTCL cancer cell antigens; and
        ii) deplete extant T cells of the patient by at least 90%;
    allowing, in the presence of the CTCL cancer cell antigens, repopulation and maturation of new T cells which recognize the CTCL cancer cell antigens; and
    providing the patient with an antigen releasing anti-cancer therapy only after a period of time sufficient to allow the repopulation and maturation of the new T cells which recognize the CTCL cancer cell antigens;
    wherein the anti-CD3 specific immunotoxin is A-dmDT390-bisFv(UCHT1), and wherein the amount administered is 20 to 60 µg/kg body weight in total dose.

2. The method of claim 1, wherein the period of time is at least three months.

3. The method of claim 1, wherein the period of time is 17 months.

4. The method of claim 1, wherein the antigen releasing anti-cancer therapy is ultraviolet (UV) radiation therapy.

5. The method of claim 1, wherein the patient achieves partial and/or complete remission in response to the treatment.

6. The method of claim 1, wherein the step of providing the patient with the antigen releasing anti-cancer therapy is repeated when CTCL recurs but the step of administering to the patient the anti-CD3 specific immunotoxin is not repeated.

7. The method of claim 1, wherein the cancer is Mycosis fungoides.

* * * * *